United States Patent
Swanepoel

(10) Patent No.: US 12,097,051 B2
(45) Date of Patent: Sep. 24, 2024

(54) METHOD AND SYSTEM FOR PREDICTING OR DETECTING CONDUCTIVE HEARING LOSS RISK IN A PERSON

(71) Applicant: HearX IP (Pty) Ltd, Ashlea Gardens (ZA)

(72) Inventor: Daniël Christiaan De Wet Swanepoel, Pretoria (ZA)

(73) Assignee: HearX IP (Pty) Ltd., Ashlea Gardens (ZA)

( * ) Notice: Subject to any disclaimer, the term of this patent is extended or adjusted under 35 U.S.C. 154(b) by 0 days.

(21) Appl. No.: 17/778,133

(22) PCT Filed: Jan. 29, 2021

(86) PCT No.: PCT/IB2021/050701
§ 371 (c)(1),
(2) Date: May 19, 2022

(87) PCT Pub. No.: WO2021/214556
PCT Pub. Date: Oct. 28, 2021

(65) Prior Publication Data
US 2023/0027720 A1    Jan. 26, 2023

Related U.S. Application Data

(60) Provisional application No. 63/012,316, filed on Apr. 20, 2020.

(51) Int. Cl.
*A61B 5/00* (2006.01)
*A61B 5/12* (2006.01)
*G16H 50/30* (2018.01)

(52) U.S. Cl.
CPC ............ *A61B 5/7275* (2013.01); *A61B 5/123* (2013.01); *G16H 50/30* (2018.01)

(58) Field of Classification Search
CPC ........... A61B 5/121; A61B 5/12; A61B 5/123; A61B 5/128; A61B 5/38
See application file for complete search history.

(56) References Cited

U.S. PATENT DOCUMENTS

| 2012/0067107 A1 | 3/2012 | Gross et al. |
| 2013/0060159 A1 | 3/2013 | Bromwich et al. |

(Continued)

OTHER PUBLICATIONS

Convery, Elizabeth1,2; Keidser, Gitte1,2; Seeto, Mark1,2; Freeston, Katrina1,2; Zhou, Dan1,2; Dillon, Harvey1,2. Identification of Conductive Hearing Loss Using Air Conduction Tests Alone: Reliability and Validity of an Automatic Test Battery. Ear and Hearing 35(1):p. e1-e8, Jan./Feb. 2014. (Year: 2014).*

(Continued)

*Primary Examiner* — Tse W Chen
*Assistant Examiner* — Michael A Catina
(74) *Attorney, Agent, or Firm* — Panitch Schwarze Belisario & Nadel LLP; Erin M. Dunston

(57) ABSTRACT

A method of, and system for, predicting conductive hearing loss risk in a person. The method includes utilizing, by using a processor, at least the following as inputs to a prediction model: (A) at least one first air conduction value for the person, and (B) any one of (a) a second air conduction value in noise for the person for in-phase binaural stimuli, or (b) a third air conduction value in noise for the person for antiphasic binaural stimuli. The method further includes predicting, by using the processor and an output of the prediction model, whether the person has a risk of conductive hearing loss. The method may be implemented without the need for bone conduction audiometry or any other clinical test to determine conductive hearing loss. The prediction model may be a logistic regression model.

18 Claims, 5 Drawing Sheets

(56) References Cited

U.S. PATENT DOCUMENTS

| | | | |
|---|---|---|---|
| 2014/0010373 A1* | 1/2014 | Gran | H04R 25/43 |
| | | | 381/23.1 |
| 2016/0113555 A1* | 4/2016 | Fausti | A61B 5/123 |
| | | | 600/559 |
| 2017/0256269 A1 | 9/2017 | Jensen et al. | |
| 2018/0160984 A1 | 6/2018 | Mauger et al. | |
| 2019/0069811 A1 | 3/2019 | Kleindienst et al. | |
| 2019/0261095 A1* | 8/2019 | Brungart | A61B 5/123 |

OTHER PUBLICATIONS

De Sousa et al., *Improving Sensitivity of the Digits-in-Noise Test Using Antiphasic Stimuli*, 41(2) Ear & Hearing 442-450 (2019).
De Sousa et al., *Pure-tone audiometry without bone-conduction thresholds: using the digits-in-noise test to detect conductive hearing loss*, 59(10) International Journal of Audiology 801-808 (Jul. 1, 2020).
Potgieter, *The South African English Smartphone Digits-in-Noise Hearing Test: Effect of Age, Hearing Loss, and Speaking Competence*, 39(4) Ear & Hearing 656-663 (Nov. 1, 2017).
Office Action with Supplementary European Search Report in corresponding European Patent Application No. 21792760.7 (issued on Nov. 18, 2022).
Convery et al., *Indentification of Conductive Hearing Loss Using Air Conduction Tests Alone: Reliability and Validty of an Automatic Test Battery*, 35.1 Ear and Hearing E1-E8 (2014).

* cited by examiner

Fig. 5

METHOD AND SYSTEM FOR PREDICTING OR DETECTING CONDUCTIVE HEARING LOSS RISK IN A PERSON

CROSS-REFERENCE TO RELATED APPLICATIONS

This application is a U.S. National Stage Application pursuant to 35 U.S.C. § 371 of International Patent Application PCT/IB2021/050701, filed on Jan. 29, 2021, and published as WO 2021/214556 on Oct. 28, 2021, which claims priority to U.S. Provisional Patent Application No. 63/012,316, filed on Apr. 20, 2020, all of which are incorporated herein by reference in their entireties for all purposes.

BACKGROUND OF THE INVENTION

THIS invention relates to a method and system for predicting conductive hearing loss risk in a patient.

Audiometry typically occurs in a sound-treated environment using air and bone conduction testing to determine the sensorineural and conductive components that may contribute to hearing loss. In these conventional test environments, bone conduction audiometry combined with air conduction audiometry detects and quantifies when a conductive component is present.

In attempts to decentralize access to hearing assessments due to costs of centralized sound-treated environments, methods have been proposed to conduct air conduction audiometry outside of a sound-treated environment with mobile solutions. Bone conduction audiometry outside a sound booth, however, remains very problematic, with significant concerns surrounding reliability due to a number of reasons including:
a) The maximum permissible ambient noise levels required for unoccluded testing is too low for reliable testing outside a sound-treated environment.
b) For self-test or home-based test offerings, setting up a bone conductor correctly is very challenging.
c) Masking dilemmas also increase the complexity and room for error for audiometric assessments with bone conduction performed outside of conventional test environments.

Hearing assessments conducted with the primary goal to fit hearing aids, as opposed to a diagnostic assessment for medical treatment, requires a reliable way to detect if there is a risk of conductive hearing loss. Traditionally bone conduction audiometry is used for this but does not inform the actual hearing aid fitting in the case of sensorineural hearing loss. If a conductive loss can be detected, a medical referral can be made to investigate underlying causes and treatment options.

Identifying alternative ways to detect or predict conductive hearing loss risk accurately for early referral, without the need for bone conduction audiometry, can enable hearing aid services to people outside of conventional test settings (e.g. people in rural communities which are located far away from any medical facilities).

The Inventor wishes to address this problem.

SUMMARY OF THE INVENTION

In accordance with a first aspect of the invention there is provided a method of predicting or determining or detecting conductive hearing loss risk in a person or patient (hereinafter only referred to as "person"), wherein the method includes:
utilizing, by using a processor, at least the following as inputs to a prediction/predictive model:
at least one first air conduction value for the person, and any one of:
a second air conduction value in noise for the person for in-phase binaural stimuli, or
a third air conduction value in noise for the person for antiphasic binaural stimuli; and
predicting, by using the processor and an output of the prediction model, whether the person has a risk of conductive hearing loss.

More specifically, the method may be a method of predicting or determining or detecting conductive hearing loss risk in a person or patient (hereinafter only referred to as "person"), without the need for bone conduction audiometry or any other clinical test to determine conductive hearing loss.

The in-phase binaural stimuli for the second air conduction value in noise refers to where a signal (e.g. a pure tone, speech or other) is presented in noise to a person, where both the signal and the noise are presented binaurally (i.e. to both ears simultaneously) and wherein the signal and noise are presented in-phase to both ears. The antiphasic binaural stimuli for the third air conduction value in noise refers to where the same signal (i.e. presented to obtain the second air conduction value) is presented in noise, but either the signal or the noise is presented out-of-phase (i.e. 180 degrees out of phase).

The prediction/predictive model may be a logistic regression model.

The utilizing step may include utilizing at least the following as inputs to the prediction model:
(i) the first air conduction value for the person,
(ii) the second air conduction value in noise for the person for in-phase binaural stimuli, and
(iii) the third air conduction value in noise for the person for antiphasic binaural stimuli.

The utilizing step may include utilizing:
the first air conduction value for the person,
the second air conduction value in noise for the person for in-phase binaural stimuli,
the third air conduction value in noise for the person for antiphasic binaural stimuli, and
a masking level difference, wherein the masking level difference refers to a difference in value between the second air conduction value and the third air conduction value, and The utilizing step may include also utilizing one or more demographic variables for the person as an input to the prediction model.

Preferably, the method may include utilising the following as inputs to the logistic regression model:
the first air conduction value for the person,
the second air conduction value and/or third air conduction value,
the masking level difference, and
the one or more demographic variables for the person.

In another variation, the method may include utilising (i) the first air conduction value for the person, (ii) the second air conduction value, and (iii) the one or more demographic variables for the person, as inputs to the logistic regression model. In other words, the third air conduction value and masking level difference need not be used as inputs and may be optional.

From the above, it should be noted that the method may utilise at least the first air conduction value for the person and either the second air conduction value or the third air conduction value in noise. In order to help increase the accuracy of the prediction, the method may include utilising:
- both the second air conduction value and the third air conduction value in noise;
- the one or more demographic variables; and/or the masking level difference.

The first air conduction value may relate to a value obtained without noise (i.e. when no noise was present when the person was tested). The first air conduction value may therefore be a signal-without-noise value. The signal presented to a person to obtain the first air conduction value may be a pure tone. The first air conduction value may therefore be a pure tone value/pure tone audiometry value, more specifically a pure tone-without noise value.

The method may specifically be implemented without the need for bone conduction audiometry or other clinical measures of middle-ear functioning like immittance measurements. More specifically the method may be for predicting whether a given/detected hearing loss of a person is conductive in nature. In this regard it should be noted that pure tone air conduction audiometry is typically the gold standard for determining hearing loss degree and configuration and if the type of hearing loss (conductive vs sensorineural) requires bone conduction in addition to air conduction pure tone audiometry.

The present method however helps to decide/predict whether it is a conductive hearing loss or a sensorineural hearing loss.

The first air conduction value may be a first air conduction threshold value for a given stimulus/signal (e.g. tone, speech or other) presented without background noise. More specifically, the first air conduction value may be a pure tone audiometry threshold value. Even more specifically, the pure tone value may be a pure tone average of a plurality/range of frequencies (e.g. 0.5, 1, 2 and 4 kHz) from/for an ear of the person (e.g. a poorer or better ear or combination of ears of the person). Alternatively, the pure tone value may be for a single frequency.

The method may include obtaining/receiving the first air conduction value from a mobile audiometer which is used on the person. The method may include utilizing a mobile audiometer on the person in order to obtain the first air conduction value. The mobile audiometer may be implemented on a mobile application (mobile app) which is installed on smart device (e.g. a smart phone or tablet) or on a computer software platform.

The method may include receiving the first air conduction value via a user interface. The user interface may be implemented on a mobile application (mobile app) which is installed on smart device (e.g. a smart phone or tablet) or on a computer software platform.

The signal for the second and third air conduction values may be a pure tone or speech. The second air conduction value may therefore be a speech recognition in noise value for in-phase binaural stimuli. Similarly, the third air conduction value may be a speech recognition in noise value for antiphasic binaural stimuli. The second air conduction value may be a speech recognition threshold (SRT) for in-phase binaural stimuli. Similarly, the third air conduction value may also be a speech recognition threshold (SRT), but for antiphasic binaural stimuli.

The method may include receiving the second air conduction value via a user interface. The method may include receiving the third air conduction value via a user interface.

The method may include, by using a processor, obtaining the second air conduction value by implementing a threshold seeking method. The threshold seeking method may be an adaptive method using digits presented in background noise, i.e. a digits-in-noise test. The method may include, by using a processor, obtaining the second air conduction value by implementing the threshold seeking method (or another threshold seeking method). The threshold seeking method may require a user to interact with the processor via a user interface. The threshold seeking method may be implemented on a mobile application (mobile app) which is installed on smart device (e.g. a smart phone or tablet) or on a computer software platform.

The one or more demographic variables for the person may include the age, gender or other descriptor of the person.

The logic regression module may be configured to calculate a probability value, by using the inputs. The method may include predicting, by using a processor, whether the person does or does not have conductive hearing loss, by comparing the calculated probability value with a reference probability value.

The logistic regression model may be configured to implement the following logistic regression formula:

$$p = \frac{1}{1 + e^{-(C_0 + (Age \times C_1) + (PTA \times C_2) + (MLD \times C_3) + (SIN \times C_4))}}$$

wherein
p refers to the probability value;
$C_0$ refers to a constant;
Age refers to the age of the person;
$C_1$ refers to an age constant;
PTA refers to the first air conduction value, more specifically the pure tone value (even more specifically the pure tone average);
$C_2$ refers to a first air conduction constant (more specifically, a pure tone value constant);
MLD refers to the masking level difference;
$C_3$ refers to a masking level difference constant;
SIN refers to the third air conduction value; and
$C_4$ refers to a third air conduction value constant (more specifically, a speech recognition threshold constant).

The method may include utilising, by using a processor, the probability value (p) in order to determine/predict whether the person has a risk of conductive hearing loss.

The method may include utilising, by using a processor, the logistic regression model in order to determine significant predictive variables.

The method may include utilising, by using a processor, the logistic regression model in order to extract a receiver operator coefficient (ROC) curve, by using the significant predictive variables.

The method may include selecting a reference probability value by utilising the ROC curve to maximize the accuracy of the prediction.

The method may include determining/predicting, by using a processor, whether the person does or does not have conductive hearing loss, by comparing the calculated probability value with a/the reference probability value.

The method may include determining/predicting, by using a processor, that the person does not have conductive hearing loss, if the calculated probability value is lower or higher (depending on how the logistic regression model is set up) than the reference probability value. The method may include determining/predicting, by using a processor, that the person may have conductive hearing loss if the calculated probability value is lower or higher (again depending on how the logistic regression model is set up) than the reference probability value.

The logistic regression model may be trained using historical hearing data. The historical hearing data may be of a plurality of people (e.g. 100 or more). The historical hearing data may include at least the following for each person of the plurality of people:
 an indication as to whether or not the person has conductive hearing loss;
 at least one first air conduction value for the person (hereinafter referred to as the "historic first air conduction value"); and
 any one of:
  a second air conduction value in noise for the person for in-phase binaural stimuli (hereinafter referred to as the "historic second air conduction value"), or
  a third air conduction value in noise for the person for antiphasic binaural stimuli (hereinafter referred to as the "historic third air conduction value").

The historical hearing data may also include the following for each person of the plurality of people:
 a masking level difference (hereinafter referred to as the "historic masking level difference"), wherein the historic masking level difference refers to a difference in value between the historic second air conduction value and the historic third air conduction value of the person; and/or
 one or more demographic variables for the person (e.g. age).

The historic first air conduction value may relate to a value obtained without noise (i.e. when no noise was present when the person was tested). The historic first air conduction value may therefore be a historic signal-without-noise value. The signal may be a pure tone. The historic first air conduction value may therefore be a historic pure tone value, more specifically a historic pure tone-without noise value.

The historic first air conduction value may be a historic first air conduction threshold value. More specifically, the historic first air conduction value may be a historic pure tone audiometry threshold value. Even more specifically, the historic pure tone value may be a pure tone average of a plurality/range of frequencies (e.g. 0.5, 1, 2 and 4 kHz) from/for an ear of the person (e.g. a poorer or better ear or combination of ears of the person). Alternatively, the pure tone value may be for a single frequency.

The in-phase binaural stimuli for the historic second air conduction value in noise refers to where a signal (e.g. a pure tone, speech or other) is presented in noise to a person, where both the signal and the noise are presented binaurally (i.e. to both ears simultaneously) and wherein the signal and noise are presented in-phase to both ears. The antiphasic binaural stimuli for the historic third air conduction value in noise refers to where the same signal (i.e. presented to obtain the historic second air conduction value) is presented in noise, but either the signal or the noise is presented out-of-phase (i.e. 180 degrees out of phase).

The signal may be a pure tone or speech. The historic second air conduction value in noise may therefore be a historic speech recognition in noise value for in-phase binaural stimuli. The historic third air conduction value in noise may therefore also be a historic speech recognition in noise value for antiphasic binaural stimuli. The historic second air conduction value in noise may be a historic speech recognition threshold (SRT) for in-phase binaural stimuli. The historic third air conduction value in noise may therefore also be a historic speech recognition threshold (SRT) for antiphasic binaural stimuli.

The method may include training the logistic regression model as described above.

The method may be implemented on a mobile app or on a computer software platform/server.

In accordance with a second aspect of the invention there is provided a system for predicting or determining or detecting conductive hearing loss risk in a person or patient (hereinafter only referred to as "person"), wherein the system includes a prediction/predictive module which is configured to implement a prediction/predictive model, wherein the prediction module is configured to utilise any two or more of the following as inputs to the prediction/predictive model:
 at least one first air conduction value for the person; and
 any one of:
  a second air conduction value in noise for the person for in-phase binaural stimuli, or
  a third air conduction value in noise for the person for antiphasic binaural stimuli,
 wherein the prediction module is configured to predict whether the person has a risk of conductive hearing loss, by utilising an output of the prediction model.

A "module", in the context of the specification, includes an identifiable portion of code, computational or executable instructions, or a computational object to achieve a particular function, operation, processing, or procedure. A module may be implemented in software, hardware or a combination of software and hardware. Furthermore, modules need not necessarily be consolidated into one device.

The in-phase binaural stimuli for the second air conduction value in noise refers to where a signal (e.g. a pure tone, speech or other) is presented in noise to a person, where both the signal and the noise are presented binaurally (i.e. to both ears simultaneously) and wherein the signal and noise are presented in-phase to both ears. The antiphasic binaural stimuli for the third air conduction value in noise refers to where the same signal (i.e. presented to obtain the second air conduction value) is presented in noise, but either the signal or the noise is presented out-of-phase (i.e. 180 degrees out of phase).

The first air conduction value may relate to a value obtained without noise (i.e. when no noise was present when the person was tested). The first air conduction value may therefore be a signal-without-noise value. The signal may be a pure tone. The first air conduction value may therefore be a pure tone value, more specifically a pure tone-without noise value.

The first air conduction value may be a first air conduction threshold value. The first air conduction value may be an air conduction pure tone audiometry value, more specifically a pure tone audiometry threshold value. Even more specifically, the pure tone value may be a pure tone average of a plurality/range of frequencies (e.g. 0.5, 1, 2 and 4 kHz) from/for an ear of the person (e.g. a poorer or better ear or combination of ears of the person). Alternatively, the pure tone value may be for a single frequency.

The signal for the second and third air conduction values may be a pure tone or speech. The second air conduction value in noise may therefore be a speech recognition in noise value for in-phase binaural stimuli. The third air conduction value in noise may also be a speech recognition in noise value for antiphasic binaural stimuli. The second air conduction value in noise may be a speech recognition threshold (SRT) for in-phase binaural stimuli. The third air conduction value in noise may be a speech recognition threshold (SRT) for antiphasic binaural stimuli.

The prediction module may be a logistic regression module. The prediction/predictive model may be a logistic regression model.

The system may be for predicting or determining conductive hearing loss risk without the need for bone conduction audiometry or any other clinical test to determine conductive hearing loss. More specifically the system may be for predicting whether a given/detected hearing loss of a person is conductive in nature.

The system may include an audiometer module which is configured to obtain/receive the first air conduction value (e.g. an air conduction pure tone value) from a mobile audiometer (e.g. which is used on the person). An example of a mobile audiometer is the so-called hearTest™ product from hearX (Pty) td). Alternatively, the audiometer module may be configured to provide a mobile audiometer functionality, in order to obtain/determine the first air conduction value. As another alternative, the audiometer module may be configured to receive the first air conduction value via a user interface.

The system, or at least part thereof, may be implemented on a mobile application (mobile app) (e.g. which can be downloaded onto a smart device of a user). The system, or at least part thereof, may be implemented in a computer program which can be installed on a computer. The system, or at least part thereof, may be implemented on an online server/platform/processing system.

Part of the system may be implemented on a mobile application and/or computer program and part of the system may be implemented on an online server/platform/processing system.

The system may include an in-noise module which is configured to obtain the second air conduction value by implementing a threshold seeking method; and/or obtain the third air conduction value by implementing the threshold seeking method (or another threshold seeking method).

The in-noise module may be a speech-in-noise (SIN) module.

Preferably, the logistic regression module may be configured to utilise the following as inputs to the logistic regression model:
the first air conduction value for the person,
the second air conduction value or third air conduction value,
a masking level difference, wherein the masking level difference refers to a difference in value between the second air conduction value and the third air conduction value, and
one or more demographic variables for the person.
, and
one or more demographic variables for the person.

The one or more demographic variables for the person may include the age of the person.

From the above, it should be noted that the logistic regression module utilises at least the first air conduction value for the person and either the second air conduction value or the third air conduction value. In order to help increase the accuracy of the logistic regression module, the module may use:
both the second air conduction value and the third air conduction value;
the one or more demographic variables; and/or
the masking level difference.

The logic regression module may be configured to calculate a probability value by using the inputs within the logistic regression model. The logic regression module may be configured to predict whether the person does or does not have conductive hearing loss, by comparing the calculated probability value with a reference probability value.

The logistic regression model may be configured to implement the following logistic regression formula:

$$p = \frac{1}{1 + e^{-(C_0 + (Age \times C_1) + (PTA \times C_2) + (MLD \times C_3) + (SIN \times C_4))}}$$

wherein
p refers to the probability value;
$C_0$ refers to a constant;
Age refers to the age of the person;
$C_1$ refers to an age constant;
PTA refers to the first air conduction value, more specifically the pure tone value (even more specifically the pure tone average);
$C_2$ refers to a first air conduction value constant;
MLD refers to the masking level difference;
$C_3$ refers to a masking level difference constant;
SIN refers to the third air conduction value; and
$C_4$ refers to a third air conduction value constant.

The logistic regression module may be configured to utilise the probability value (p) in order to determine/predict whether the person has a risk of conductive hearing loss.

The logistic regression module may be configured to utilise the logistic regression model in order to determine significant predictive variables.

The logistic regression module may be configured to extract a receiver operator coefficient (ROC) curve (i.e. for the logistic regression model), by using the significant predictive variables.

The logistic regression module may be configured to select a reference probability value by utilising the ROC curve.

The logistic regression module may be configured to determine/predict that the person does not have conductive hearing loss, if the probability value is lower or higher than the reference probability value (depending on the direction of the model). The logistic regression module may be configured to determine/predict that the person may have conductive hearing loss if the probability value is lower or higher than the reference probability value (depending on the direction of the model).

The logistic regression model may be trained using historical hearing data. The historical hearing data may be of a plurality of people (e.g. 100 or more). The historical hearing data may include any two or more of the following for each person of the plurality of people:
an indication as to whether or not the person has conductive hearing loss;
at least one historic first air conduction value for the person (hereinafter referred to as the "historic pure tone value");
a historic second air conduction value in noise for the person for in-phase binaural stimuli;
a third air conduction value in noise for the person for antiphasic binaural stimuli;
a masking level difference (hereinafter referred to as the "historic masking level difference"), wherein the historic masking level difference refers to a difference in value/threshold between the historic second air conduction value and historic third air conduction value of the person; and one or more demographic variables for the person (e.g. age).

The in-phase binaural stimuli for the historic second air conduction value in noise refers to where a signal (e.g. a pure tone, speech or other) is presented in noise to a person, where both the signal and the noise are presented binaurally (i.e. to both ears simultaneously) and wherein the signal and noise are presented in-phase to both ears. The antiphasic binaural stimuli for the historic third air conduction value in noise refers to where the same signal (i.e. presented to obtain the second air conduction value) is presented in noise, but either the signal or the noise is presented out-of-phase (i.e. 180 degrees out of phase).

The system, preferably a training module of the system, may be configured to train the logistic regression model as described above by using the historical hearing data.

BRIEF DESCRIPTION OF THE DRAWINGS

The invention will now be described, by way of example, with reference to the accompanying diagrammatic drawings. In the drawings:

FIG. 5 shows a table in which various probability reference values, together with their associated sensitivity and specificity (more specifically "1-specificity") values (as illustrated in the graph in FIG. 4) are set out for the logistic regression model of the system.

DESCRIPTION OF PREFERRED EMBODIMENTS

Figure 1:
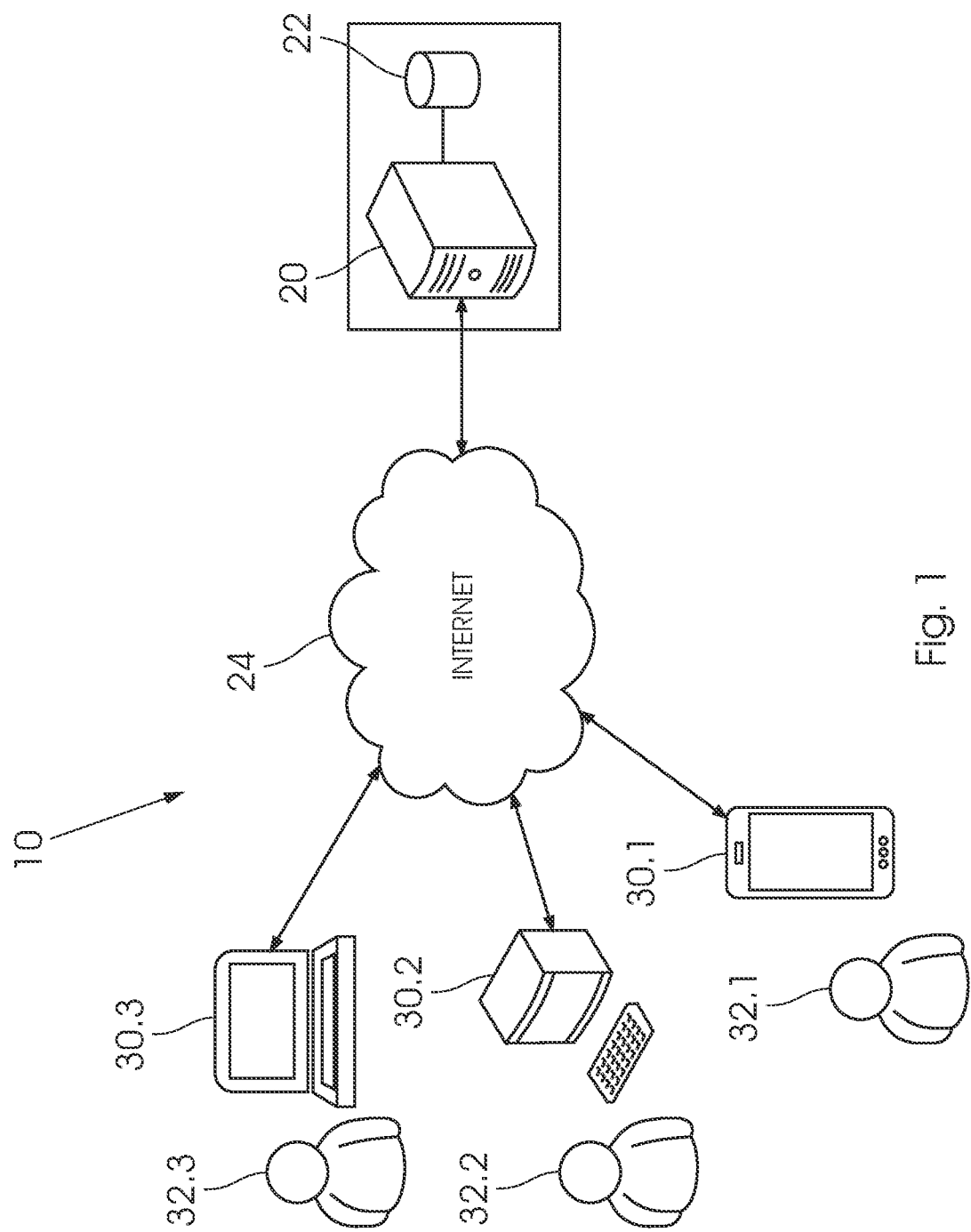
FIG. 1 shows a schematic layout of a system for predicting/determining conductive hearing loss risk in a person/patient, in accordance with the invention.
Figure 2:
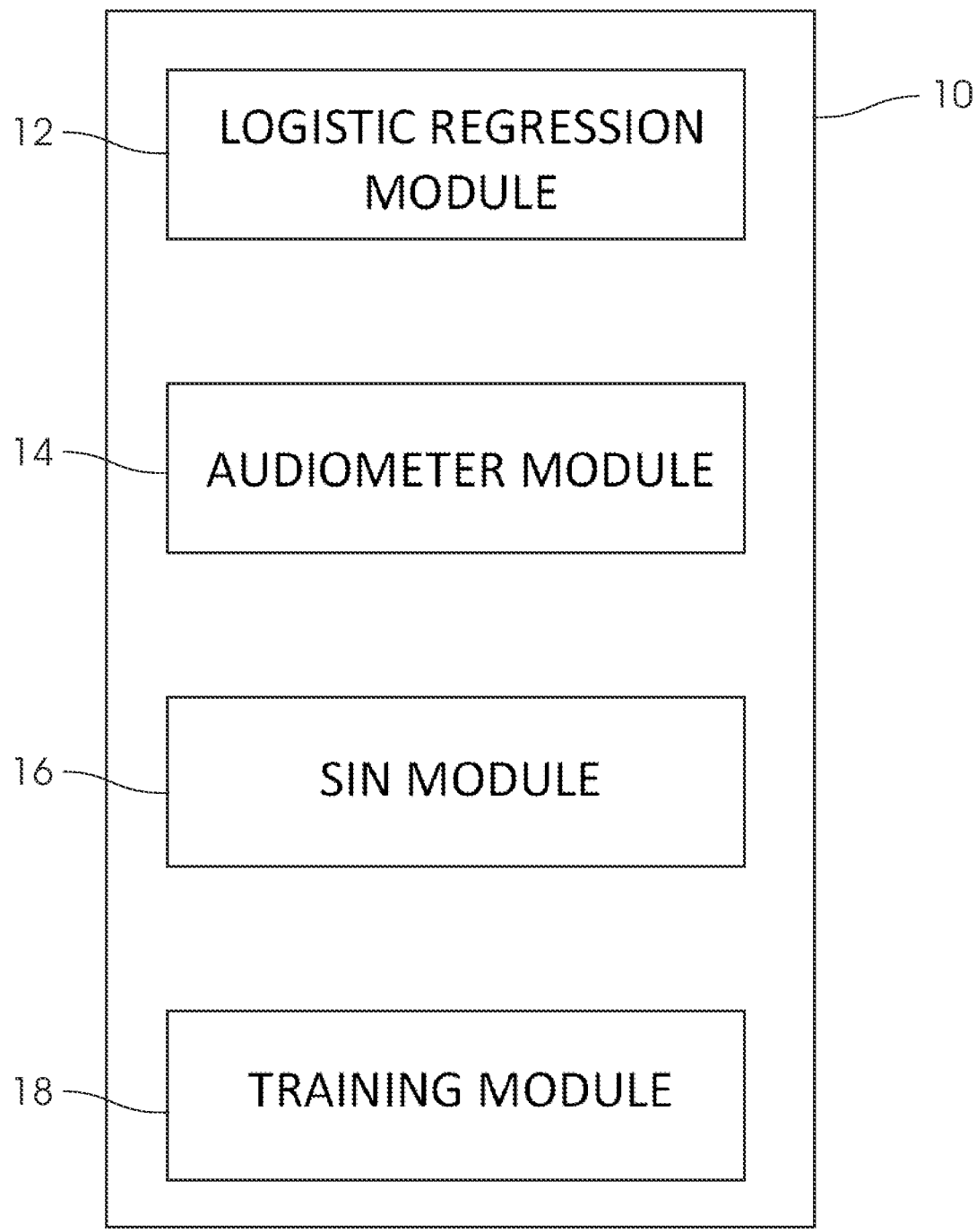
FIG. 2 shows a functional layout of the system shown in FIG. 1.

The present invention relates to a method and system for predicting/determining the presence of conductive hearing loss in a person without the need to conduct bone conduction audiometry or other measures like tympanometry. In the drawings, reference numeral 10 refers generally to the system in accordance with the invention.

The system 10 utilises a logistic regression approach that combines a series/plurality of hearing test results and one or more demographic variable/indicators to predict the risk of conductive hearing loss. More specifically, the test results are used as inputs to a logistic regression model which is implemented by a logistic regression module 12 of the system 10.

The tests used to perform this approach are procedures that can typically be employed outside of conventional test environments (i.e. clinics and sound booths) and can be performed as a series of self-tests. These test results include:
a) a first air conduction value for the person;
b) a second air conduction value in noise for the person for in-phase binaural stimuli;
c) a third air conduction value in noise for the person for antiphasic binaural stimuli,
d) a masking level difference, wherein the masking level difference refers to a difference in value/threshold between the second air conduction value and the third air conduction value, and
e) one or more demographic variables for the person, such as age.

It should be noted that the system 10, in essence, only requires the use of:
the first air conduction value, and
either the second air conduction value in noise or the third air conduction value in noise.

However, for improved accuracy, both the second air conduction value and the third air conduction value, as well as the masking level difference and/or the one or more demographic variables (mentioned in (d) and (e) above) can be used. These features are however optional.

The first air conduction value, more specifically, is an air conduction pure tone audiometry value/pure tone threshold value. The pure tone audiometry value may, more specifically, be a pure tone average of a plurality/range of frequencies from/for an ear of the person (e.g. a poorer or better ear or combination of ears of the person) or it may be for a single frequency.

The in-phase binaural stimuli for the second air conduction value in noise refers to where a signal (e.g. a pure tone, speech or other) is presented in noise to a person, where both the signal and the noise are presented binaurally (i.e. to both ears simultaneously) and wherein the signal and noise are presented in-phase to both ears. The antiphasic binaural stimuli for the third air conduction value in noise refers to where the same signal (i.e. presented to obtain the second air conduction value) is presented in noise, but either the signal or the noise is presented out-of-phase (i.e. 180 degrees out of phase).

Each of these test results is described further below in more detail.

In the description below:
i. the first air conduction value is an air conduction pure tone audiometry value/pure tone threshold value;
ii. the second air conduction value is a speech recognition threshold value for in-phase binaural stimuli (hereinafter referred to as the "in-phase speech recognition value"); and
iii. the third air conduction value is a speech recognition threshold value for anti-phasic binaural stimuli (hereinafter referred to as the "antiphasic speech recognition value");

It should however be noted that the invention is not limited to only these specific types of values and stimuli described below (i.e. the specific types of values and signals/stimuli described below are merely examples).

(a) Test for Pure Tone Threshold Value

In order to obtain a pure tone threshold value, more specifically a pure tone audiometry threshold across of range of frequencies, a mobile audiometer can be used. In this regard, the mobile audiometer can typically be used in a self-test mode which requires no test operator. An example of a mobile audiometer which can be used is the so-called hearTest™ product from hearX (Pty) Ltd.

The mobile audiometer can be implemented on a mobile app which is installed on a smart device 30.1 or a software program which is installed on a computer 30.2, 30.3, of a user 32.1-32.3 (collectively hereinafter referred to as 32). The system 10 can therefore include an audiometer module 14 (e.g. provided within a mobile app or software program) which is configured to implement this particular test.

During this test, pure tones are typically presented at set intensities across a range of frequencies. A person responds by pressing a button (e.g. on the mobile phone) when a tone is heard. By tracking down in intensity a threshold seeking method is applied (e.g. ISO shortened-ascending method) to determine an intensity where a sound is heard 50% of the time. The pure tone average of certain frequencies (e.g. 0.5, 1, 2 and 4 kHz) from an ear (poorer or better ear) can be used as input data.

(b) & (c) Inphase and Antiphasic Speech Recognition Values

The antiphasic speech recognition value more specifically refers to a speech recognition threshold (SRT) in noise, expressed as a decibel signal-to-noise ratio (SNR), when antiphasic binaural stimuli is used. Similarly, in-phase speech recognition value more specifically refers to a speech recognition threshold in noise, expressed as a decibel signal-to-noise ratio, when in-phase binaural stimuli is used.

A speech signal is typically presented to a person in the presence of background noise and expressed as a signal-to-noise ratio (i.e. −5 dB SNR). A threshold seeking method is then applied to approximate the level at which 50% of the speech signals are correctly identified. Usually an adaptive up-down-intensity threshold seeking method can be used, which is based on whether the signal was identified correctly or incorrectly. This value is reported as the speech recognition threshold (SRT) expressed in dB SNR. The digits-in-noise test is a well-known, rapid self-test that allows for determining the speech recognition threshold binaurally for both antiphasic and in-phase speech stimuli. This self-test can be implemented on a mobile app which is installed on a smart device 30.1 or a software program which is installed on a computer 30.2, 30.3, of a user 32. The system 10 can therefore include a speech-in-noise (SIN) module 16 (e.g. provided within a mobile app or software program) which is configured to implement this particular self-test.

(d) Masking Level Difference

For this test, the difference in decibels between the antiphasic speech recognition value and the in-phase speech recognition value (see tests (b)&(c) above) is determined. This difference reflects the so-called masking level difference. The digits-in-noise thresholds for antiphasic and in-phase stimuli can therefore be subtracted from each other to provide a masking level difference result.

(e) Demographic Variable(s)

In this example, the demographic variable used is age. Other demographic variables could however also be used.

Development of Logistic Regression Model

One way of combining the test results above would be to use a person's (i) age, (ii) pure tone average of thresholds for 0.5, 1, 2 and 4 kHz in the poorer ear; (iii) antiphasic digits-in-noise speech recognition threshold, and (iv) masking level difference constituting the difference between speech recognition thresholds using antiphasic and in-phase binaural digits-in-noise (DIN) testing.

The logistic regression model can use the following general logistic regression formula (p being a probability value):

$$p = \frac{1}{1 + e^{-(b_0 + b_1 x_1 + b_2 x_2 + \ldots + b_p x_p)}}$$

Figure 3:
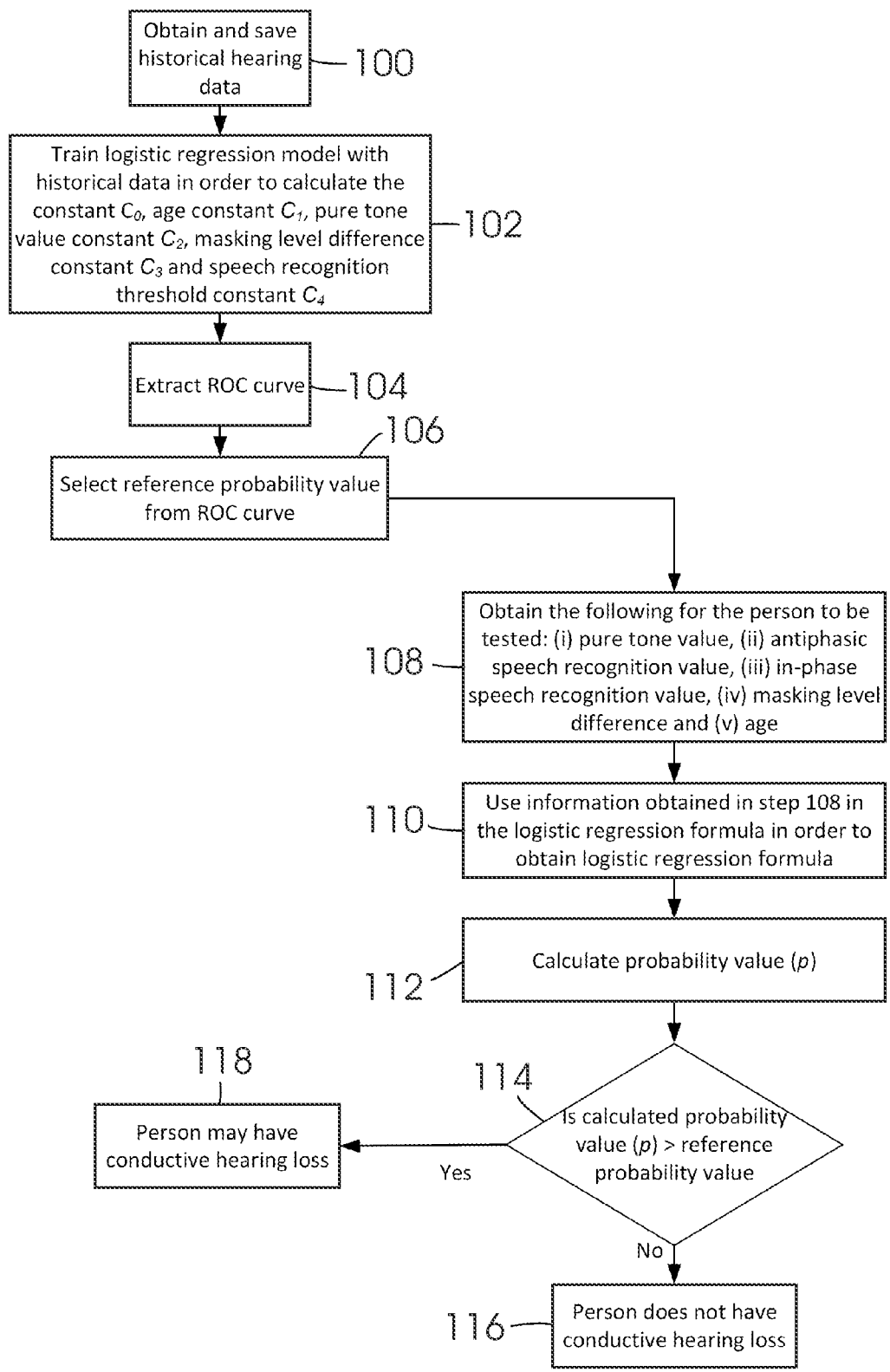
FIG. 3 shows a flow diagram which illustrates a general process flow of the system shown in FIG. 1.

The logistic regression model can be developed/trained, in software (e.g. by a training module 18), from an existing dataset of patients with sensorineural hearing loss and conductive hearing loss (i.e. historical hearing data) who have been assessed by:
 i. pure tone air conduction audiometry;
 ii. speech-in-noise testing using antiphasic and in-phase binaural testing; and
 iii. derived masking level difference scores calculated as the difference between the speech recognition threshold obtained for the antiphasic and in-phase binaural speech-in-noise test (see FIG. 3, block 100).

In addition to (i)-(iii) above, the ages of the patients are also taken into account by the training module 18 for developing/training the logistic regression formula.

Through the above development/training (see FIG. 3, block 102), the following logistic regression formula/equation is created/developed:

$$p = \frac{1}{1 + e^{-(C_0 + (Age \times C_1) + (PTA \times C_2) + (MLD \times C_3) + (SIN \times C_4))}} \tag{1}$$

wherein
 p refers to a probability value;
 $C_0$ refers to a constant;
 Age refers to the age of the person;
 $C_1$ refers to an age constant;
 PTA refers to the pure tone value (more specifically the pure tone average expressed in decibel)
 $C_2$ refers to a pure tone value constant;
 MLD refers to the masking level difference (MLD)(expressed as decibel);
 $C_3$ refers to a masking level difference constant;
 SIN refers to the antiphasic speech recognition threshold (SRT) (expressed as decibel (dB) signal-to-noise (SNR) ratio); and
 $C_4$ refers to a speech recognition threshold constant.

The constants $C_0$-$C_4$ are calculated in software during the training/development phase when the existing dataset (i.e. the historical hearing data) of patients is used.

Once the logistic regression formula has been created/developed, the logic regression module 12 utilises the logistic regression formula/model in order to determine significant predictive variables. These significant predictive variables are then used by the logistic regression module 12 in order to extract a receiver operator coefficient (ROC) curve (see graph 50 in FIG. 4, as well as FIG. 3, block 104). The measure of an area under the curve (AUROC) is then an indication of the logistic regression model's accuracy. Further accuracy measures which can also be determined by the logistic regression module 12 include sensitivity, specificity and overall accuracy of the model on the existing database of patients used to develop the logistic regression formula/equation.

To determine an optimal probability value ("reference probability"), the ROC curve can be used to select a cut-off, reference probability value which maximizes the sensitivity and specificity of the model (see FIG. 3, block 106). Once this probability has been added to the logistic regression module 12, the equation can be used to predict whether new cases have a conductive hearing loss or not.

The test results for a particular person can then be used by the logistic regression module 12 as variables in the logistic regression equation (1). If the calculated/obtained probability value (p) is smaller or larger (depending on the direction of the model) than the reference probability, then a conductive hearing loss is predicted.

As mentioned before, the system 10 can be implemented in a variety of different ways. For example, all the modules 12, 14, 16, 18 of the system 10 can be incorporated into a computer program/software which can be installed on a computer 30.2, 30.3. In this example the system 10 would not necessarily need a service/processing unit 20 (described later on in the specification).

In another example, all the modules 12, 14, 16, 18 of the system 10 can be incorporated into a mobile app which can be downloaded onto a smart device (e.g. smart phone 30.1 or tablet).

In a further example, all the modules 12, 14, 16, 18 of the system 10 can be incorporated into a central server/processing unit 20. In this example, users 32 would then typically use their smart phones 30.1 or computers 30.2, 30.3 to communicate with the server 20, via the Internet 24, in order to utilize the modules 12, 14, 16, 18, so that a person can find out whether he/she (or someone else) might have conductive hearing loss.

In yet a further example, the functions of the modules 12, 14, 16, 18 could be split between (i) the server 20 and (ii) the mobile app and computer software which is installable onto the smart devices 30.1 and computers 30.2, 30.3 of users 32. In other words, one or more of the modules 12, 14, 16, 18 could be implemented on the server 12 (for example module 12 and 18), while the other modules (e.g. modules 14 and 16) are implemented within the mobile app and computer software which are installed on the smart devices 30.1 and computers 30.2, 30.3 of the users 32. It should however be appreciated that the functions of the modules 12, 14, 16, 18 can be split in any manner between (i) the server 12 and (ii) the mobile app and computer program.

For the sake of completeness it is mentioned that in examples where only the in-phase speech recognition threshold is used and the masking level difference and antiphasic speech recognition threshold are not used, those parts of the formula (as set out in formula (1) above) would effectively fall away. In other words, the adjusted formula would then be:

$$p = \frac{1}{1 + e^{-(C_0 + (Age \times C_1) + (PTA \times C_2) + (IST \times C_5))}} \quad (2)$$

where
IST refers to the in-phase speech recognition threshold, and
C5 refers to an in-phase speech recognition threshold constant.

EXAMPLE 1

In this example, the training of the logistic regression model is described, as well as how the trained model is then used when assessing a particular person for possible conductive hearing loss.

In this example, the data of 130 adult subjects was stored on a database 22 and used for training purposes (see FIG. 3, block 100). Of the 130 subjects, 30 had conductive hearing loss and 100 had sensorineural hearing loss. In this example the subjects received pure tone audiometry assessments and speech-in-noise testing using antiphasic and in-phase digits in noise tests.

Using logistic regression analysis, a predictive, logistic regression model was then developed/trained to predict a person's risk of conductive hearing loss versus sensorineural hearing loss (see FIG. 3, block 102). More specifically, by running a logistic regression on the data stored on the database 40 of subjects using poorer ear PTA (PEPTA), antiphasic SRT, MLD and age as input variables with conductive hearing loss (n (total number of subjects with conductive hearing loss)=30) and sensorineural hearing loss (n (total number of subjects with sensorineural hearing loss)=100) as output binary variables, provides the following results:
Overall accuracy of 93.8%
$C_0 = -8.315$
$C_1 = -0.140$
$C_2 = 0.162$
$C_3 = -1.102$
$C_4 = -0.852$ These values can then be incorporated by the logistic regression module 12 into equation (1):

$$p = \frac{1}{1 + e^{-(-8.315 + (Age \times (-0.140)) + (PTA \times 0.162) + (MLD \times (-1.102)) + (SIN \times (-0.852)))}}$$

Figure 4:
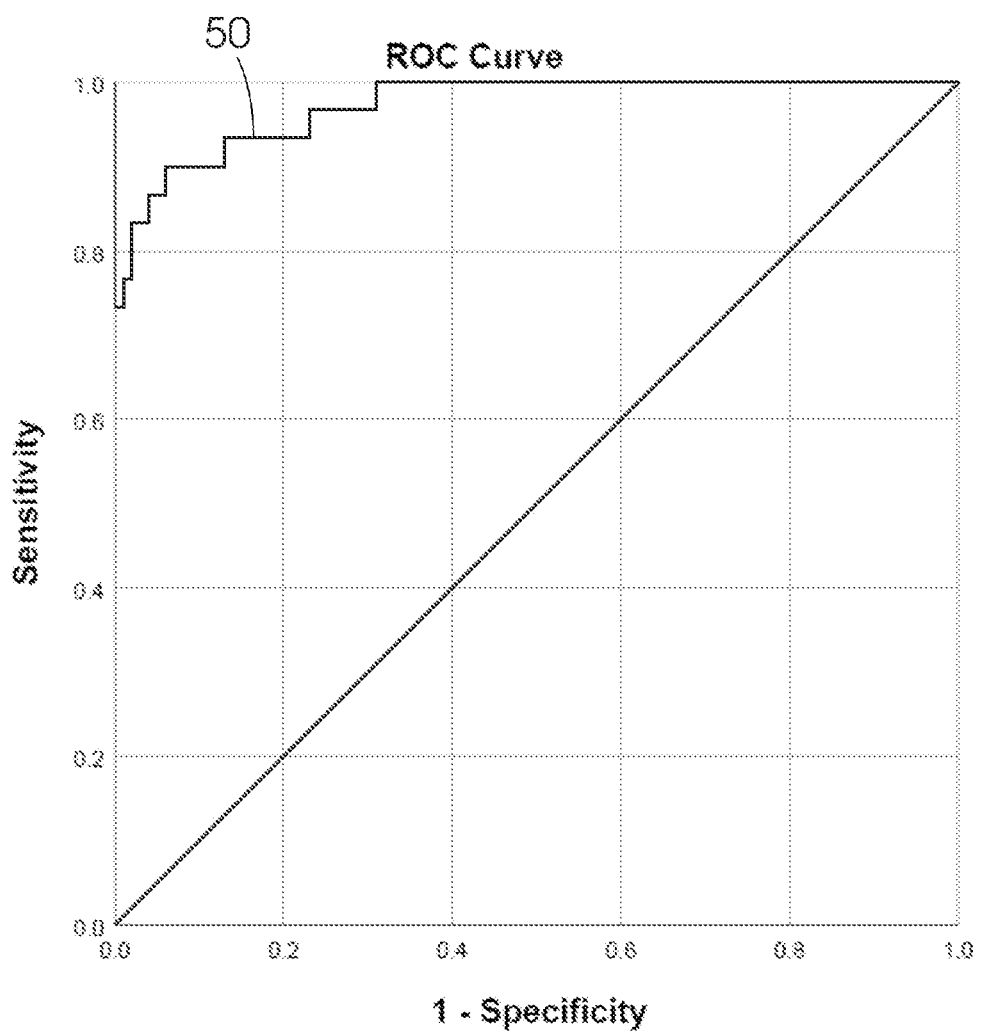
FIG. 4 shows a graphical illustration of an ROC curve which is extracted from a logistic regression model implemented by the system shown in FIG. 1.

The logistic regression module 12 is configured to extract a receiver operator coefficient (ROC) curve (see graph 50 in FIG. 4, as well as FIG. 3, block 104). To determine the optimal probability value (probability reference value), the logistic regression module 12 utilises the ROC curve (see graph 50 in FIG. 4, as well as FIG. 3, block 106). More specifically, this ROC curve is used to select a cut-off probability reference value which maximizes the sensitivity and specificity of the model.

Figure 5:
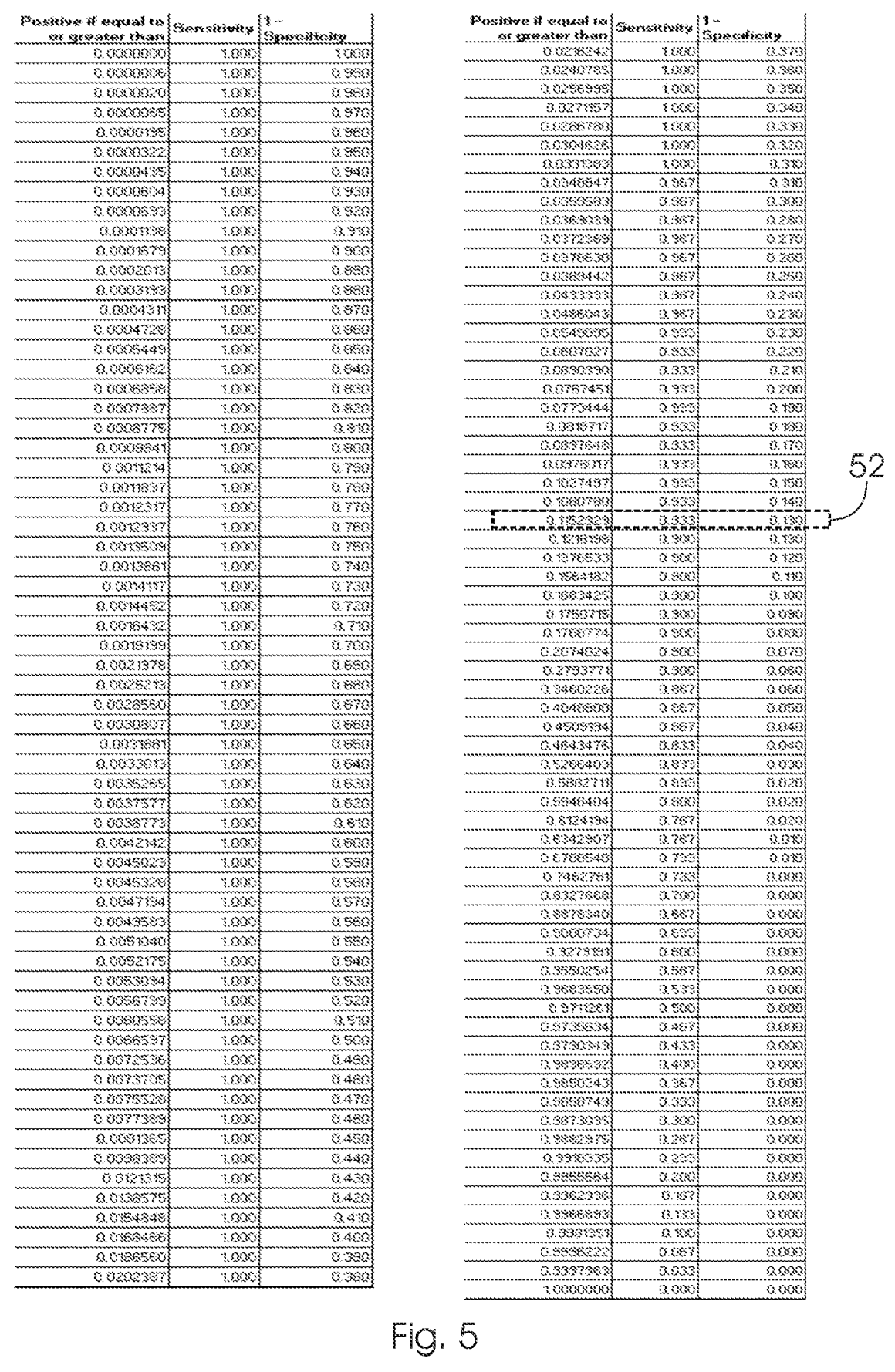

In this regard, FIG. 5 shows a table in which various probability reference values, together with their associated sensitivity value and specificity value (more specifically "1−specificity" value) are set out for the logistic regression model of the system.

In this example, the probability reference value is selected to be 0.1152929, which has a sensitivity of 0.933 and a specificity of 0.87 (i.e. 1−0.130) (see reference numeral 52). Thus, if any calculated probability value is equal to, or greater than, 0.1152929, then the logistic regression module 12 determines/predicts that the person may have conductive hearing loss.

Once this probability has been added to the logistic regression, the equation can be used to predict whether new cases have a conductive hearing loss or not. The test inputs required from these new cases would be used as variables in the logistic regression equation and if the obtained probability value is larger than the reference probability, then a conductive hearing loss is predicted.

To test the logistic regression module 12, a person with the following input data is used (see FIG. 3, blocks 108 and 110):
Age=35 years
PTA=32 dB
MLD=6.3 dB
Antiphasic SRT (i.e. SIN)=−14.3 dB SNR $$p = \frac{1}{1 + e^{-(-8.315 + (35 \times (-0.140)) + (32 \times 0.162) + (6.3 \times (-1.102)) + ((-14.3) \times (-0.852)))}}$$

Thus, p=0.057867 (see FIG. 3, block 112)

Since the calculated value of p (probability value) is less than the probability reference value of 0.1152929, the logistic regression module 12 determines/predicts that that the person does not have a conductive hearing loss risk (see FIG. 3, blocks 114, 116 and 118).

EXAMPLE 2

This example describes how the system 10 can be implemented in practice, where the logistic regression module 12 and training module 18 are implemented on the server 20, while the audiometer module 14 and SIN module 16 are implemented in a mobile app and computer program which can be downloaded onto a smart device 30.1 and computer 30.2, 30.3 of a user 32. In this example, specific reference will be made where a user 32.1 has downloaded the mobile app onto his/her smart device 30.1. It should however be appreciated that the same also applies to when a user 32.2, 32.3 installs the computer program on his/her computer 30.2, 30.2.

In order to allow a user 32.1 to utilise the logistic regression module 12, the user would utilise the mobile app installed on his smart phone 30.1, in order to communicate with the server 12 via the Internet 24. More specifically, the mobile app is configured to instruct a user 32.1 (e.g. via a user interface) to perform a test by using a mobile audiometer (i.e. the audiometer module 14), which is typically implemented within the mobile app and coupled with earphones which can be plugged into the smart phone 30.1, in order to allow the test to be performed. The user 32.1 can then allow the audiometer module 14 to conduct the test in order to calculate a pure tone average (PTA) of certain frequencies (e.g. 0.5, 1, 2 and 4 kHz) from an ear of the user 32.1 (e.g. a poorer or better ear). In a slight alternative embodiment, the mobile app can be configured to allow the user 32.1 to input the pure tone average of the selected frequencies via the user interface.

The mobile app is also further configured to instruct the user 32.1, via the user interface, to perform a speech-in-noise (SIN) test (more specifically a digit-in-nose test) which is implemented by the mobile app, more specifically the SIN module 16. Earphones can again be used in order to allow the test to be performed. By conducting this test, the antiphasic speech recognition threshold and in-phase speech recognition threshold can be calculated by the SIN module 16, as well as the masking level difference.

In a slight alternative embodiment, the mobile app can be configured to allow the user 32.1 to input the pure tone average of the selected frequencies via the user interface.

In addition to the above, the mobile app is also configured to prompt the user 32.1 to enter certain demographic details, such as his/her age, on the user interface.

Once the audiometer test and SIN test have been performed, and the age of the user 32.1 has been entered, the mobile app sends these details to the server 20. Upon receiving the details, the logistic regression module 12 determines/predicts (in the manner as described earlier) whether the user 32.1 may have conductive hearing loss (hereinafter referred to as the "hearing loss result"). The server 20 then sends the hearing loss result back to the mobile app which then displays the result on the user interface (i.e. on a display screen of the smart phone 30.1).

In this example, the server 20 essentially acts as a software-as-a-service (SAAS) model which receives information from the mobile app, calculates a hearing loss result, and sends the result back to the user 32.1. In order for a user 32.1 to use this facility provided by the server 20, the server may require the user 32.1 to log in. In other words, only users which are registered with the server 20 would be able to utilise the facility. As mentioned before, the logistic regression module 12 could also be implemented on the mobile app, in which case it would not be necessary for the user 32.1 to have Internet connectivity to use the invention.

The Inventor believes that the present invention provides an effective and easy to use way of predicting whether a person has conductive hearing loss, without the need for bone conduction audiometry or other clinical measures of middle-ear functioning. As a result, the invention can be used in remote locations (e.g. in rural communities) where there are no audiometry testing rooms, which are usually required when testing for conductive hearing loss with bone conduction audiometry.

The invention claimed is:

1. A method of determining whether a person has conductive hearing loss, wherein the method includes:
    (a) conducting an air conduction audiometry test on the person in order to obtain at least one first air conduction value for the person;
    (b) conducting any one of:
        an in-noise audiometry test with in-phase binaural stimuli on the person in order to obtain a second air conduction value in noise for the person for in-phase binaural stimuli, or
        an in-noise audiometry test with antiphasic binaural stimuli on the person in order to obtain a third air conduction value in noise for the person for antiphasic binaural stimuli;
    (c) utilizing, by using a processor, at least the following as inputs to a trained prediction model:
        the at least one first air conduction value for the person, and any one of:
            the second air conduction value in noise for the person for in-phase binaural stimuli, or
            the third air conduction value in noise for the person for antiphasic binaural stimuli;
    (d) determining, by using the processor and an output of the prediction model, whether the person has conductive hearing loss; and
    communicating a hearing loss result obtained from the determining whether the person has conductive hearing loss to a user by (i) displaying the hearing loss result on a display screen and/or (ii) sending the hearing loss result via a communication device to a smart device or to a computer of the user,
    wherein the prediction model is trained using historical hearing data.

2. The method of claim 1, wherein the method is a method of determining whether the person has conductive hearing loss, without the need for bone conduction audiometry or any other clinical test to determine conductive hearing loss.

3. The method of claim 2, wherein the prediction model is a logistic regression model.

4. The method of claim 3,
    wherein element (b) includes
        conducting an in-noise audiometry test with in-phase binaural stimuli on the person in order to obtain the second air conduction value in noise for the person for in-phase binaural stimuli, and
        conducting an in-noise audiometry test with antiphasic binaural stimuli on the person in order to obtain the third air conduction value in noise for the person for antiphasic binaural stimuli,
    wherein the element (c) includes utilizing at least the following as inputs to the prediction model:
        (i) the first air conduction value for the person,
        (ii) the second air conduction value in noise for the person for in-phase binaural stimuli, and
        (iii) the third air conduction value in noise for the person for antiphasic binaural stimuli.

5. The method of claim 4, where in the utilizing step includes utilizing:
    the first air conduction value for the person,
    the second air conduction value in noise for the person for in-phase binaural stimuli, the third air conduction value in noise for the person for antiphasic binaural stimuli, and a masking level difference, wherein the masking level difference refers to a difference in value between the second air conduction value and the third air conduction value.

6. The method of claim 3, wherein the utilizing step includes also utilizing one or more demographic variables for the person as an input to the prediction model.

7. The method of claim 3, wherein the first air conduction value relates to a value obtained without noise and the first air conduction value is therefore a signal-without-noise value.

8. The method of claim 7, wherein the first air conduction value relates to a value obtained without noise and through utilization of a pure tone, and the first air conduction value is therefore a pure tone-without noise value.

9. The method of claim 3, wherein the method includes conducting the air conduction audiometry test of element (a) by utilizing a mobile audiometer which is used on the person; and conducting any one of the in-noise audiometry test with in-phase binaural stimuli or the in-noise audiometry test with antiphasic binaural stimuli in element (b) by utilizing the mobile audiometer.

10. The method of claim 3, wherein the second air conduction value is a speech recognition threshold (SRT) for in-phase binaural stimuli.

11. A system for determining whether a person has conductive hearing loss, wherein the system includes:
one or more processors configured to execute code that cause the execution of operations including:
a) conducting an air conduction audiometry test on the person in order to obtain at least one first air conduction value for the person, and
b) conducting any one of
an in-noise audiometry test with in-phase binaural stimuli on the person in order to obtain a second air conduction value in noise for the person for in-phase binaural stimuli, or
an in-noise audiometry test with antiphasic binaural stimuli on the person in order to obtain a third air conduction value in noise for the person for antiphasic binaural stimuli;
c) implementing a prediction model, wherein the prediction model is configured to utilize at least the following as inputs to the prediction model:
the at least one first air conduction value for the person; and
any one of:
the second air conduction value in noise for the person for in-phase binaural stimuli, or
the third air conduction value in noise for the person for antiphasic binaural stimuli,
wherein the prediction model has been trained using historical hearing data and is configured to determine whether the person has a risk of conductive hearing loss, by utilizing an output of the prediction model, and
d) communicating a hearing loss result determined by the prediction model to a user by (i) displaying the hearing loss result on a display screen and/or (ii) sending it via a communication network to a smart device or to a computer of the user.

12. The system of claim 11, wherein the system is for determining whether the person has conductive hearing loss without the need for bone conduction audiometry.

13. The system of claim 11, wherein the prediction model is a logistic regression model.

14. The system of claim 13, wherein the logistic regression model is configured to utilize the following as inputs:
the first air conduction value for the person,
the second air conduction value or third air conduction value,
a masking level difference, wherein the masking level difference refers to a difference in value between the second air conduction value and the third air conduction value, and
one or more demographic variables for the person.

15. The system of claim 14, wherein the first air conduction value relates to a value obtained without noise and is therefore a signal-without-noise value.

16. The system of claim 15, further including a mobile audiometer which incorporates at least one processor of the one or more processors, wherein the at least one processor is configured to execute portions of the code corresponding to operations a) and b.

17. The system of claim 13, wherein the logic regression model is configured to calculate a probability value by using the inputs within the logistic regression model, and wherein the logic regression model is configured to determine whether the person does or does not have conductive hearing loss, by comparing the calculated probability value with a reference probability value.

18. The system of claim 11, wherein the historical hearing data includes at least the following for each person of a plurality of people:
an indication as to whether or not the person has conductive hearing loss;
at least one first air conduction value for the person; and
any one of:
a second air conduction value in noise for the person for in-phase binaural stimuli, or
a third air conduction value in noise for the person for antiphasic binaural stimuli.

* * * * *